(12) United States Patent
Imamoto et al.

(10) Patent No.: US 7,649,117 B2
(45) Date of Patent: Jan. 19, 2010

(54) PROCESS OF PREPARING OPTICALLY ACTIVE β-HYDROXYCARBOXYLIC ACID DERIVATIVE

(75) Inventors: Tsuneo Imamoto, Chiba (JP); Kazuhiro Yoshida, Chiba (JP); Miwako Nishimura, Chiba (JP); Aya Koide, Chiba (JP)

(73) Assignees: National University Corporation Chiba University, Chiba-Shi (JP); Nippon Chemical Industrial Co., Ltd., Tokyo (JP)

( * ) Notice: Subject to any disclaimer, the term of this patent is extended or adjusted under 35 U.S.C. 154(b) by 0 days.

(21) Appl. No.: 12/179,088

(22) Filed: Jul. 24, 2008

(65) Prior Publication Data
US 2009/0030231 A1    Jan. 29, 2009

(30) Foreign Application Priority Data
Jul. 26, 2007    (JP) .............................. 2007-195233

(51) Int. Cl.
*C07C 45/65*    (2006.01)
(52) U.S. Cl. ...................... 568/312; 568/343; 568/392; 568/433; 568/458
(58) Field of Classification Search ................. 568/312, 568/343, 392, 433, 458
See application file for complete search history.

(56) References Cited

U.S. PATENT DOCUMENTS

| 4,933,482 A | 6/1990 | Sayo et al. |
| 2007/0021610 A1 | 1/2007 | Imamoto et al. |

FOREIGN PATENT DOCUMENTS

WO    WO 2007/123957 A2    11/2007

OTHER PUBLICATIONS

United Kingdom Office Action dated Nov. 26, 2008, issued in corresponding United Kingdom Patent Application No. GB0813270.6.
Imamoto, Tsuneo et al.; "t-Bu-QuinoxP Ligand: Applications in Asymmetric Pd-Catalyzed Allylic Substitution and Ru-Catalyzed Hydrogenation"; Journal of Organic Chemistry, vol. 72(19), pp. 7413-7416, 2007.
Fox, Martin E. et al; "Bis-(2,5-diphenylphosholanes) with $sp^2$ Carbon Linkers: Synthesis and Application in Asymmetric Hydrogenation"; Journal of Organic Chemistry, vol. 73(3), pp. 775-784, 2008.
Imamoto, Tsuneo et al.; "Air-stable P-Chiral Bidentate Phosphine Ligand with (1-Adamantyl)methylphosphino Group"; Chemistry Letters, vol. 36(4), pp. 500-501, 2007.
Imamoto, Tsuneo et al.; "An Air-Stable P-Chiral Phosphine Ligand for Highly Enantloselective Transition-Metal-Catalyzed Reactions"; Journal of American Chemical Society, vol. 127(34), pp. 11934-11935, 2005.
Noyori et al., "Asymmetric Hydrogenation of β-Keto Carboxylic Esters. A Practical, Purely Chemical Acess to β-Hydroxy Esters in High Enantiomeric Purity", J. Am. Chem. Soc. 1987, 109, pp. 5856-5858.
Yamano et al., "Enantioselective Hydrogenation of β-Keto Esters Catalyzed by P-Chiral Bis(dialkylphosphino)ethanes-Ru(II)", Tetrahedron Letters 40 (1999), pp. 2577-2580.
Genêt et al., "Practical Asymmetric Hydrogenation of β-Keto Esters at Atmospheric Pressure using Chiral Ru (II) Catalysts", Tetrahedron Letters, 1995, vol. 36, No. 27, pp. 4801-4804.

*Primary Examiner*—Sikarl A Witherspoon
(74) *Attorney, Agent, or Firm*—Westerman, Hattori, Daniels & Adrian, LLP

(57) ABSTRACT

Disclosed is a process of preparing an optically active β-hydroxycarboxylic acid derivative comprising asymmetrically hydrogenating a β-keto compound in the presence of a catalyst comprising a transition metal complex compound having a 2,3-bis(dialkylphosphino)pyrazine derivative as a ligand. The pyrazine derivative is preferably a quinoxaline derivative, and the transition metal is preferably ruthenium. Preferred examples of the quinoxaline derivative are (S,S)-2,3-bis(tert-butylmethylphosphino)quinoxaline, (R,R)-bis(tert-butylmethylphosphino)quinoxaline, (S,S)-bis(tert-adamantylmethylphosphino)quinoxaline, and (R,R)-bis(adamantylmethylphosphino)quinoxaline.

3 Claims, No Drawings

PROCESS OF PREPARING OPTICALLY ACTIVE β-HYDROXYCARBOXYLIC ACID DERIVATIVE

TECHNICAL FIELD

This invention relates to a process of preparing an optically active β-hydroxycarboxylic acid derivative that is important as an intermediate for pharmaceuticals, agricultural chemicals, or physiologically active substances, for example, very useful as an intermediate for synthesizing antibiotics.

BACKGROUND ART

Processes that are known or thought to be useful for the production of an optically active β-hydroxycarboxylic acid derivative include (1) once synthesizing a racemic form of a desired β-hydroxycarboxylic acid derivative, followed by optical resolution using an optically active resolving agent or an enzyme, (2) starting with an asymmetric compound, or (3) using an asymmetric catalyst.

The process (1) is exemplified by a process using an enzyme to achieve optical resolution of a racemate. For example, only one of the optical isomers of a racemic esterified β-hydroxycarboxylic acid derivative may selectively be hydrolyzed by using lipase.

The process (1) which uses an optically active resolving agent requires an equivalent or more amount of a resolving agent relative to a β-hydroxycarboxylic acid derivative. Moreover, complicated procedures such as crystallization, separation, and purification, are involved before obtaining an optically active β-hydroxycarboxylic acid derivative. The process (1) which uses an enzyme, while capable of yielding a β-hydroxycarboxylic acid derivative with relatively high optical purity, limits the type of a reaction substrate and the absolute configuration of a resulting β-hydroxycarboxylic acid derivative.

The process (2) is conceivable but problematic in that an optically active starting compound is not only expensive but must be used in a stoichiometric excess.

As the process (3), detailed researches have recently been done into catalytic asymmetric synthesis of an optically active β-hydroxycarboxylic acid derivative that can achieve high efficiency and asymmetric yield. For example, U.S. Pat. No. 4,933,482A discloses a process of preparing an optically active β-hydroxycarboxylic acid derivative. The process comprises asymmetrically hydrogenating a β-keto compound using a 2,2'-bis(diphenylphosphino)-1,1'-binaphthyl)ruthenium complex (BINAP-Ru catalyst). The process is very useful in that a β-hydroxycarboxylic acid derivative having high optically purity can be prepared under mild conditions. However, the process involves reacting for a relatively long time such as several tens of hours under a hydrogen pressure of 5 to 40 atm.

SUMMARY OF THE INVENTION

In the light of the above circumstances, it is an object of the invention to provide a process of preparing an optically active β-hydroxycarboxylic acid derivative using a versatile and yet highly active catalyst.

As a result of extensive studies on catalytic asymmetric synthesis of an optically active β-hydroxycarboxylic acid derivative, the present inventors have found that asymmetric hydrogenation of a β-keto compound in the presence of a specific catalyst produces a desired optically active β-hydroxycarboxylic acid derivative with the reduced number of steps at high efficiency in good asymmetric yield. The present invention has been reached based on this finding.

The invention provides a process of preparing an optically active β-hydroxycarboxylic acid derivative represented by formula (III):

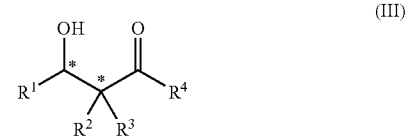

wherein $R^1$, $R^2$, and $R^3$, which may be the same or different, each represent a hydrogen atom, an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, or a substituted aromatic heterocyclic group;

$R^4$ has the same meaning as $R^1$, $R^2$, or $R^3$ or represents a group comprising an oxygen atom and the group which is represented by $R^1$, $R^2$, or $R^3$ and is bonded to the oxygen atom, or represents an amino group or a substituted amino group; and the asterisk * indicates an asymmetric center.

The process comprises asymmetrically hydrogenating a β-keto compound represented by formula (I):

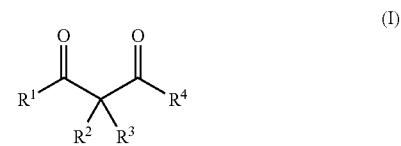

wherein $R^1$, $R^2$, $R^3$, and $R^4$ are as defined above.

in the presence of a catalyst comprising a transition metal complex compound having a pyrazine derivative represented by formula (II) shown below as a ligand.

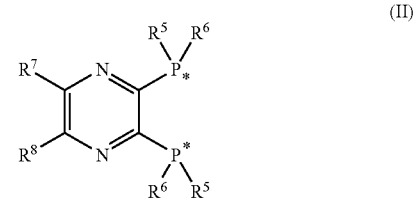

wherein $R^5$ and $R^6$, which may be the same or different, each represent an alkyl group or a substituted alkyl group;

$R^7$ and $R^8$, which may be the same or different, each have the same meaning as $R^1$, $R^2$, and $R^3$, or $R^7$ and $R^8$ are taken together to form a fused ring; and the asterisk * is as defined above.

DETAILED DESCRIPTION OF THE INVENTION

The β-keto compound that can be used as a starting material in the process of the invention is represented by formula (I). The optically active β-hydroxycarboxylic acid derivative obtained by the process of the invention is represented by formula (III). The groups represented by $R^1$, $R^2$, and $R^3$ in formulae (I) and (III) will be described.

The term "alkyl group" includes straight-chain or branched alkyl groups having 1 to 6 carbon atoms, such as methyl, ethyl, n-propyl, 2-propyl, n-butyl, 2-butyl, isobutyl, tert-butyl, n-pentyl, 2-pentyl, tert-pentyl, 2-methylbutyl, 3-methylbutyl, 2,2-dimethylpropyl, n-hexyl, 2-hexyl, 3-hexyl, tert-hexyl, 2-methylpentyl, 3-methylpentyl, 4-methylpentyl, and 5-methylpentyl.

The term "substituted alkyl group" includes the above recited alkyl groups at least one hydrogen atom of which is displaced with a substituent, such as an alkyl group, a cycloalkyl group, an alkoxy group, a halogen atom, an amino group, or a protected amino group. Any protective group known for the protection of an amino group can be used. Examples of the amino protective group are described, e.g., in *Protective Groups in Organic Synthesis,* 2nd Ed., John Wiley & Sons, Inc. Examples of useful amino protective groups include an alkyl group, a cycloalkyl group, an aralkyl group, an acyl group, and an alkyloxycarbonyl group.

The term "cycloalkyl group" includes a cycloalkyl group having 3 to 16 carbon atoms, such as cyclopropyl, cyclobutyl, cyclopentyl, cyclohexyl, cycloheptyl, 2-methylcyclopentyl, 3-methylcyclopentyl, cycloheptyl, 2-methylcyclohexyl, 3-methylcyclohexyl, and 4-methylcyclohexyl. The term "cycloalkyl group" also includes a polycyclic alkyl group, such as menthyl, bornyl, norbornyl, or adamantyl.

The substituted cycloalkyl group includes the above described cycloalkyl groups at least one hydrogen atom of which is displaced with a substituent such as an alkyl group, a cycloalkyl group, an alkoxy group, a halogen atom, an amino group or a protected amino group.

The term "aralkyl group" includes aralkyl groups having 7 to 12 carbon atoms, such as benzyl, 2-phenylethyl, 1-phenylpropyl, 2-phenylpropyl, 3-phenylpropyl, 1-phenylbutyl, 2-phenylbutyl, 3-phenylbutyl, 4-phenylbutyl, 1 -phenylpentyl, 2-phenylpentyl, 3-phenylpentyl, 4-phenylpentyl, 5-phenylpentyl, 1-phenylhexyl, 2-phenylhexyl, 3-phenylhexyl, 4-phenylhexyl, 5-phenylhexyl, and 6-phenylhexyl.

The substituted aralkyl group includes the above described aralkyl groups at least one hydrogen atom of which is displaced with a substituent such as an alkyl group, a cycloalkyl group, a halogenated alkyl group, an alkoxy group, a halogen atom, an amino group, or an alkyl-substituted amino group.

The term "aryl group" includes aryl groups having 6 to 14 carbon atoms, such as phenyl, naphthyl, and anthryl.

The substituted aryl group includes the above described aryl groups at least one hydrogen atom of which is displaced with a substituent such as an alkyl group, a cycloalkyl group, a halogenated alkyl group, an alkoxy group, a halogen atom, an amino group, or an alkyl-substituted amino group and the above described aryl groups adjacent two hydrogen atoms of which are displaced with a substituent such as an alkylenedioxy group.

The "aliphatic heterocyclic group" is preferably 5- or 6-membered. The aliphatic heterocyclic group includes one containing 1 to 3 hetero atoms such as nitrogen, oxygen, and sulfur atoms. Examples of the aliphatic heterocyclic group include pyrrolidy-2-one, piperidino, piperazinyl, morpholino, tetrahydrofuryl, and tetrahydropyranyl.

The term "substituted aliphatic heterocyclic group" includes the above described aliphatic heterocyclic groups at least one hydrogen atom of which is displaced with a substituent such as an alkyl group, a cycloalkyl group, a halogenated alkyl group, an alkoxy group, or a halogen atom.

The term "aromatic heterocyclic group" preferably includes 5- or 6-membered, monocyclic or polycyclic aromatic heterocyclic rings containing 1 to 3 hetero atoms such as nitrogen, oxygen, and sulfur atoms. Examples of the aromatic heterocyclic group include pyridyl, imidazolyl, thiazolyl, furfuryl, pyranyl, furyl, benzofuryl, and thienyl.

The "substituted aromatic heterocyclic group" includes the above described aromatic heterocyclic groups at least one hydrogen atom of which is displaced with a substituent such as an alkyl group, a cycloalkyl group, a halogenated alkyl group, an alkoxy group, or a halogen atom.

The group represented by $R^4$ in formulae (I) and (III) is described below. $R^4$ has the same meaning as $R^1$, $R^2$, or $R^3$. $R^4$ also represents a group comprising (a) a hydrogen atom or the group represented by $R^1$, $R^2$, or $R^3$, and (b) an oxygen atom. In this case $R^4$ is bonded to the carbonyl group via the oxygen atom. $R^4$ also represents an amino group or a substituted amino group.

Examples of the group comprising the hydrogen atom or the group represented by $R^1$, $R^2$, or $R^3$, and an oxygen atom include a hydroxyl group, a methoxy group, an ethoxy group, a phenyloxy group, a benzyloxy group, and a p-methoxybenzyloxy group.

When $R^4$ is selected from the same atom and the same groups as $R^1$, $R^2$, and $R^3$ to be different from $R^1$, it is selected from alkyl groups bulkier than $R^1$ so that the keto group nearer to $R^1$ may be reduced more preferentially. Examples of such bulky alkyl groups include isopropyl, tert-butyl, 2,2,4,4-tetramethylbutyl, adamantyl, and norbornyl.

The term "substituted amino group" includes an amino group at least one hydrogen of which is displaced with a substituent such as an alkyl group, a cycloalkyl group, a halogenated alkyl group, an alkoxy group, or a halogen atom.

In formulae (I) and (III), $R^1$, $R^2$, and $R^3$ may be the same or different. When $R^4$ is an alkyl group, it may be the same as one or more than one of $R^1$, $R^2$, and $R^3$. $R^1$, $R^2$, $R^3$, and $R^4$ may be independent of each other, or two or more of them may be crosslinked to each other.

Specific examples of the β-keto compound represented by formula (I) include methyl acetoacetate, ethyl acetoacetate, isopropyl acetoacetate, n-butyl acetoacetate, n-pentyl acetoacetate, n-hexyl acetoacetate, n-heptyl acetoacetate, n-octyl acetoacetate, ethyl 2-methylacetoacetate, methyl 3-oxopentanoate, methyl 3-oxohexanoate, methyl 3-oxoheptanoate; ethyl 3-oxooctanoate, ethyl 3-oxononanoate, ethyl 3-oxodecanoate, ethyl 3-oxo-3-phenylpropanoate, ethyl 3-oxo-3-(p-methylphenyl)propanoate, ethyl 3-oxo-3-(p-methoxyphenyl)propanoate, ethyl 3-oxo-3-(3,4-dimethoxyphenyl)-propanoate, ethyl 3-oxo-3-(p-boromophenyl)propanoate, ethyl 3-oxo-3-(p-chlorophenyl)propanoate, ethyl 3-oxo-3-(p-fluorophenyl)propanoate, ethyl 4-phenyl-3-oxobutanoate, methyl 5-phenyl-3-oxopentanoate, ethyl 4-hydroxy-3-oxobutanoate, methyl 4-benzyloxy-3-oxobutanoate, and ethyl 4-benzyloxy-3-oxobutanoate.

The groups represented by $R^5$ and $R^6$ in formula (II) are described below. The alkyl group and the substituted alkyl group as $R^5$ and $R^6$ are exemplified by the same examples as recited for $R^1$, $R^2$, and $R^3$. $R^5$ and $R^6$ may be the same or different. Although $R^5$ and $R^6$ may be independent of each other or crosslinked to each other, it is essential to select $R^5$ and $R^6$ so as to result in asymmetry on the phosphorus atom or to make the phosphorus atom constitute a point of the symmetry plane of axial asymmetry.

In order to effectively induce asymmetry on the phosphorus atom, it is preferred that $R^5$ and $R^6$ are selected so as to make a large difference in three-dimensional bulkiness therebetween. Examples of preferred combination of $R^5$ and $R^6$ are a combination of a methyl group and a tert-butyl group and a combination of a methyl group and an adamantyl group.

In order to make the phosphorus atom constitute a point of the symmetry plane of axial asymmetry, it is preferred that the moiety providing the asymmetry on $R^5$ and $R^6$ is as close as possible to the phosphorus atom so as to effectively induce the asymmetry. This is exemplified by a configuration in which $R^5$ and $R^6$ are crosslinked to each other, and an atomic group including the crosslinked moiety and the phosphorus atom is 2,5-dimethylphospholane.

The group represented by $R^7$ and $R^8$ in formula (II) is then described. As stated, $R^7$ and $R^8$ have the same meaning as $R^1$, $R^2$, and $R^3$. $R^7$ and $R^8$ may be the same or different. $R^7$ and $R^8$ may be taken together to form a fused ring. Examples of the fused ring include a benzene ring, a naphthalene ring, a phenanthrene ring, a methylenedioxy ring, an ethylenedioxy ring, and a cyclohexane ring.

It is particularly preferred that $R^7$ and $R^8$ are taken together to form a benzene ring. In this case, the pyrazine derivative represented by formula (II) is a quinoxaline derivative represented by formula (IV):

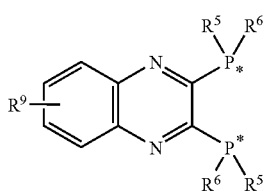

(IV)

wherein $R^5$, $R^6$, and the asterisk * are as defined above; and $R^9$ represents a monovalent substituent.

Examples of the monovalent substituent represented by $R^9$ in formula (IV) include an alkyl group, a cycloalkyl group, a halogenated alkyl group, an alkoxy group, a halogen atom, an amino group, a protected amino group, and a nitro group. The benzene ring may have one or more than one substituents $R^9$. When there are two or more substituents $R^9$, they may be either the same or different.

Examples of the pyrazine derivative of formula (II) having asymmetry introduced at the phosphorus atom are shown below.

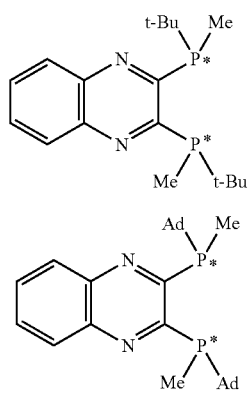

(a): (S,S)-2,3-Bis(tert-butylmethylphosphino)quinoxaline or (R,R)-2,3-Bis(tert-butylmethylphosphino)quinoxaline
(b): (S,S)-2,3-Bis(adamantylmethylphosphino)quinoxaline or (R,R)-2,3-Bis(adamantylmethylphosphino)quinoxaline Examples of the pyrazine derivative of formula (II) in which the phosphorus atom constitutes a point of symmetry plane of axial asymmetry as shown below.

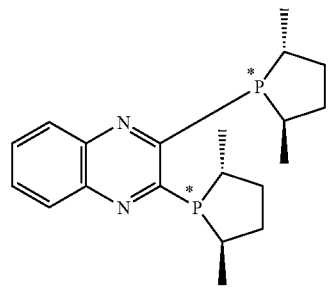

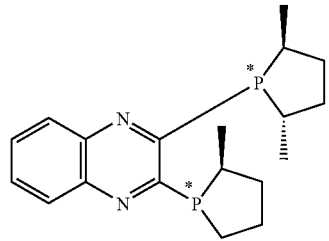

(c): 2,3-Bis[(R,R)-2,5-dimethylphospholano]quinoxaline
(d): 2,3-Bis[(S,S)-2,5-dimethylphospholano]quinoxaline The pyrazine derivatives of formula (II) including the quinoxaline derivatives of formula (IV) can be prepared in accordance with the process disclosed in commonly assigned U.S. Patent Application 2007/0021610A1, the disclosure of which is incorporated herein by reference.

The pyrazine derivative of formula (II) including the quinoxaline derivative of formula (IV) reacts with a transition metal to form a complex compound, which can be used as a catalyst for asymmetric synthesis. Examples of the transition metal with which to form a complex include rhodium, ruthenium, iridium, palladium, nickel, and iron. Preferred of them are the group VIII elements, such as rhodium, ruthenium, iridium, palladium, and nickel. Ruthenium is particularly preferred. A ruthenium complex having the pyrazine derivative of formula (II) as a ligand can be prepared by, for example, mixing a pyrazine derivative of formula (II) and a ruthenium compound having benzene or substituted benzene coordinated to a ruthenium atom, e.g., $[RuCl_2(\eta^6\text{-}C_6H_6)]_2$.

The catalyst comprising the transition metal complex compound is preferably used in an amount of 0.0001 to 100 mol %, more preferably 0.001 to 10 mol %, based on the reaction substrate. To promote the reaction moderately while suppressing the amount of the catalyst, an even more preferred amount of the catalyst to be used is 0.02 to 5 mol %.

The asymmetric hydrogenation reaction is usually carried out in a solvent commonly employed in general organic chemical reactions, such as toluene, hexane, tetrahydrofuran (THF), diethyl ether, dioxane, acetone, ethyl acetate, chlorobenzene, dimethylfornamide (DMF), acetic acid, and water. Preferred solvents are methanol, ethanol, and dichloromethane.

The amount of the solvent to be used is decided appropriately, taking into consideration the fluidity of the reaction mixture during the reaction and the effects the solvent exerts on the reaction. Where the reaction proceeds well without a solvent, for example, when the reactant mixture to be reacted is a low-viscosity, homogeneous fluid with no aid of a solvent, it is not necessary to use a solvent.

The asymmetric hydrogenation reaction temperature is preferably −80° C. to 150° C., more preferably 0° C. to 120° C. in which range the reaction is promoted while suppressing a side reaction and racemization.

The asymmetric hydrogenation reaction is preferably carried out for a period of from one minute to one month, more preferably a period of from 3 hours to 3 days, which period is adequate for completion of the reaction.

The β-hydroxycarboxylic acid derivative synthesized by the process of the invention can be used in the form of a reaction mixture as obtained. If desired, the reaction mixture may be subjected to usual work-up and purification procedures such as solvent removal, liquid-liquid separation, crystallization, distillation, sublimation, and column chromatography.

The preparation process of the invention may be performed either batchwise or continuously.

The optically active β-hydroxycarboxylic acid derivative obtained by the process of the invention is used as an intermediate for pharmaceuticals, agricultural chemicals, and physiologically active substances. For example, it is useful as an intermediate for synthesis of antibiotics.

EXAMPLES

The present invention will now be illustrated in greater detail with reference to Examples, but it should be understood that the invention is not construed as being limited thereto.

All the synthesis operations in Examples were carried out using thoroughly dried glassware. The reaction was performed in an argon or nitrogen atmosphere. A commercially available phosphine ligand, (R,R)-2,3-bis(tert-butylmethylphosphino)quinoxaline ((R,R)-t-Bu-QuinoxP*), from Sigma-Aldrich Japan, was used as such. The solvent and the metal compound such as $[RuCl_2(\eta^6-C_6H_6)]_2$ were general reagents.

NMR spectrum measurement was performed using an NMR spectrometer from JEOL, Ltd. ($^1$H: 300 MHz; $^{13}$C: 75.4 MHz; $^{31}$P: 121.4 MHz). Tetramethylsilane ($^1$H) was used as an internal standard. GC analysis was performed using GC-14B FID detector from Shimadzu Corp. Mass spectrometry was conducted using GC-MS from Shimadzu Corp.

Example 1

Synthesis of ethyl (S)-3-hydroxy-3-phenylpropionate

In 0.5 ml of dried and degassed DMF were dissolved 4.9 mg (15 μmol) of (R,R)-t-Bu-QuinoxP*(1) and 3.4 mg (6.7 μmol) of $[RuCl_2(\eta^6-C_6H_6)]_2$ in a nitrogen atmosphere. The mixture was heated at 100° C. for 10 minutes. After cooling to 50° C., the solvent was removed by evaporation under reduced pressure to give a catalyst as a reddish to purple solid. The resulting catalyst was dissolved in 3 ml of degassed ethanol in a glove box. To the solution was added a solution of 129 mg (0.67 mmol) of ethyl 3-oxo-3-phenylpropionate in 1 ml of dichloromethane, and the mixture was transferred into a stainless steel autoclave. After purging the autoclave with hydrogen four times, hydrogen was introduced into the autoclave to 20 atm. The reaction mixture in the autoclave was stirred at 50° C. for 24 hours. After cooling to room temperature, hydrogen gas was released from the autoclave. The solvent was removed, and the residue was dissolved in diethyl ether. The resulting solution was washed successively with water and a sodium chloride aqueous solution, and the organic layer was dried over anhydrous sodium sulfate. Any volatile matter was removed by evaporation, and the residue was purified by silica gel column chromatography to give the title compound, ethyl (S)-3-hydroxy-3-phenylpropionate.

Examples 2 to 12

Various β-hydroxycarboxylic acid derivatives were synthesized in the same manner as in Example 1, except for altering the substrate, hydrogen pressure, temperature, and so forth as shown in Table 1 below. The results obtained are shown in Table 1 together with the results of Example 1. Unless otherwise specified, the reaction system was ketone/t-Bu-QuinoxP*(1)/$[RuCl_2(\eta^6-C_6H_6)]_2$/EtOH/$CH_2Cl_2$=0.67 mmol/0.015 mmol/0.0067 mmol/3.0 ml/1.0 ml, and the amount of Ru was 2 mol %.

TABLE 1

Synthesis of β-Hydroxycarboxylic Acid Derivative

| Example No. | R$^1$ | R$^2$ | H$_2$ (atm) | Temp. (° C.) | Yield*$^1$ (%) | % ee*$^2$ (Abs. Config.*$^3$) |
|---|---|---|---|---|---|---|
| 1 | Ph | OEt | 20 | 50 | 89 (6a) | 99.3 (S) |
| 2 | 4-MeC$_6$H$_4$ | OEt | 20 | 70 | 94 (6b) | 98.9 (S) |
| 3 | 4-MeOC$_6$H$_4$ | OEt | 50 | 70 | 73 (6c)*$^4$ | 99.3 (S) |
| 4 | 4-BrC$_6$H$_4$— | OEt | 20 | 70 | 87 (6d) | 99.5 (S) |
| 5 | 4-ClC$_6$H$_4$ | OEt | 20 | 70 | 88 (6e) | 99.9 (S) |
| 6 | 4-FC$_6$H$_4$ | OEt | 50 | 70 | 93 (6f) | 99.8 |
| 7*$^5$ | 3,4-dimethoxyphenyl | OEt | 100 | 70 | 82 (6g)*$^4$ | 99.8 |
| 8 | Me | OMe | 20 | 50 | >99 (6h)*$^6$ | 99.7 (R) |
| 9 | ClCH$_2$ | OEt | 20 | 50 | 96 (6i) | 99.2 |
| 10 | Me | NMe$_2$ | 20 | 50 | 94 (6j)*$^7$ | 97 |
| 11 | Me | t-Bu | 20 | 50 | 93 (6k)*$^7$ | 99.0 |
| 12*$^8$ | Ph | OEt | 100 | 100 | 50 (6a) | 95 (S) |

Note:
*$^1$Isolation yield
*$^2$Measured by chiral HPLC or chiral GC analysis.
*$^3$Determined by comparing the chiral HPLC or chiral GC results with literature data.
*$^4$Racemic ethyl 3-ethoxy-3-arylpropionate was by-produced, to which the low yield seemed ascribed.
*$^5$16 hours
*$^6$Conversion yield determined by $^1$H-NMR analysis.
*$^7$NMR yield determined by using 1,4-bis(trimethylsilyl)benzene as an internal standard.
*$^8$Ethyl 3-oxo-3-phenylpropionate/t-Bu-QuinoxP*(1)/$[RuCl_2(\eta^6-C_6H_6)]_2$/EtOH/$CH_2Cl_2$ = 6.0 mmol/0.00132 mmol/0.00060 mmol/3.0 ml/1.0 ml; Ru, 0.02 mol %; 48 hours According to the process of the present invention, an optically active β-hydroxycarboxylic acid with high optical purity can be produced with the reduced number of steps using a small amount of a catalyst, and an optically active β-hydroxycarboxylic acid derivative can be produced efficiently in good asymmetric yield. The catalyst used in the process of the invention achieves excellent catalytic activity and enantio- and diastereoselectivity. The optically active β-hydroxycarboxylic acid derivative obtained by the process of the invention is important as an intermediate for pharmaceuticals, agricultural chemicals, and physiologically active substances. For example, it is very useful as an intermediate for synthesizing antibiotics. Thus, the present invention is of very high industrial utility.

What is claimed is:

1. A process of preparing an optically active-hydroxycarboxylic acid derivative represented by formula (III):

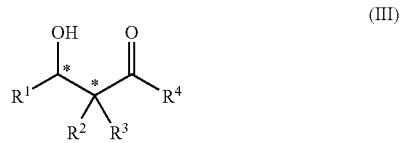

(III)

wherein $R^1$ represents an aryl group, a substituted aryl group or a substituted alkyl group in which at least one hydrogen atom of an alkyl group is displaced with a halogen atom;

$R^2$ and $R^3$, which may be the same or different, each represent a hydrogen atom, an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, or a substituted aromatic heterocyclic group; $R^4$ has the same meaning as $R^1$, $R^2$, or $R^3$ or represents a group comprising an oxygen atom and the group which is represented by $R^1$, $R^2$, or $R^3$ and is bonded to the oxygen atom, or represents an amino group or a substituted amino group; and the asterisk * indicates an asymmetric center, comprising asymmetrically hydrogenating a β-keto compound represented by formula (I):

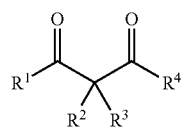

(I)

wherein $R^1$, $R^2$, $R^3$, and $R^4$ are as defined above, in the presence of a catalyst comprising a ruthenium complex compound having a pyrazine derivative represented by formula (II) shown below as a ligand:

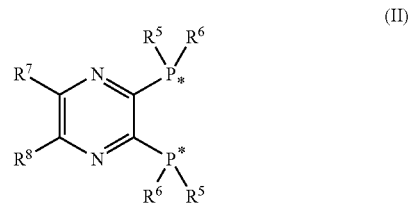

(II)

wherein $R^5$ and $R^6$, which may be the same or different, each represent an alkyl group or a substituted alkyl group; $R^7$ and $R^8$, which may be the same or different, each have the same meaning as $R^1$, $R^2$, and $R^3$, or $R^7$ and $R^8$ are taken together to form a fused ring; and the asterisk * is as defined above.

2. The process according to claim 1, wherein the pyrazine derivative represented by formula (II) is a quinoxaline derivative represented by formula (IV):

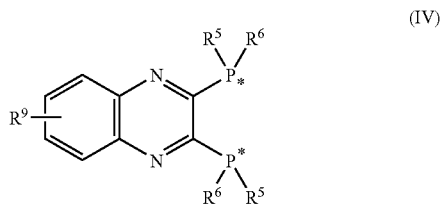

(IV)

wherein $R^5$, $R^6$, and * are as defined above, and $R^9$ represents a monovalent substituent.

3. The process according to claim 1, wherein the substituted aryl group is an aryl group in which at least one hydrogen atom is displaced with a halogen atom.

* * * * *